US007955266B2

(12) United States Patent
Casula et al.

(10) Patent No.: US 7,955,266 B2
(45) Date of Patent: Jun. 7, 2011

(54) ULTRASONIC CONTACT TRANSDUCER WITH MULTIPLE EMITTING ELEMENTS AND MEANS OF BRINGING THESE ELEMENTS INTO CONTACT

(75) Inventors: Olivier Casula, Clahart (FR); Gérard Cattiaux, Chateaufort (FR)

(73) Assignees: Commissariat a l'Energie Atomique, Paris (FR); Institut de Radioprotection et de Surete Nucleaire, Clamart (FR)

( * ) Notice: Subject to any disclaimer, the term of this patent is extended or adjusted under 35 U.S.C. 154(b) by 743 days.

(21) Appl. No.: 10/579,657

(22) PCT Filed: Nov. 16, 2004

(86) PCT No.: PCT/FR2004/050589

§ 371 (c)(1),
(2), (4) Date: May 17, 2006

(87) PCT Pub. No.: WO2005/050617

PCT Pub. Date: Jun. 2, 2005

(65) Prior Publication Data

US 2007/0167800 A1 Jul. 19, 2007

(30) Foreign Application Priority Data

Nov. 17, 2003 (FR) ...................................... 03 50842

(51) Int. Cl.
*A61B 8/14* (2006.01)
*G01N 29/24* (2006.01)
*H04R 17/00* (2006.01)

(52) U.S. Cl. ........ 600/459; 367/138; 367/155; 367/128; 310/334

(58) Field of Classification Search .................. 600/444, 600/459, 472
See application file for complete search history.

(56) References Cited

U.S. PATENT DOCUMENTS

| | | | | | |
|---|---|---|---|---|---|
| 4,166,395 | A | * | 9/1979 | Dannehl | 73/634 |
| 4,437,468 | A | * | 3/1984 | Sorenson et al. | 600/459 |
| 5,485,263 | A | * | 1/1996 | Bjorner et al. | 356/4.01 |
| 5,680,863 | A | | 10/1997 | Hossack et al. | |
| 5,913,825 | A | | 6/1999 | Watanabe et al. | |
| 6,424,597 | B1 | * | 7/2002 | Bolomey et al. | 367/138 |
| 6,578,424 | B1 | * | 6/2003 | Ziola et al. | 73/632 |

FOREIGN PATENT DOCUMENTS

| | | |
|---|---|---|
| DE | 10043199 A1 | 9/2002 |
| JP | 57-075640 | 5/1982 |

(Continued)

OTHER PUBLICATIONS

International Search Report, for International Application No. PCT/FR2004/050589, date mailed May 27, 2005.

(Continued)

*Primary Examiner* — Long V Le
*Assistant Examiner* — Helene Bor
(74) *Attorney, Agent, or Firm* — Nixon Peabody LLP

(57) ABSTRACT

Ultrasonic contact transducer with multiple ultrasonic emitting elements and means of bringing these elements into contact.

This transducer is applicable particularly to non-destructive testing and comprises means (8, 10) for bringing elements (2) into contact with an object (6) to be checked and means (26, 28, and 34 to 40) of determining the positions of elements relative to the object, using means bringing elements into contact, to determine delay laws to be applied to excitation pulses of the elements, to generate a focussed ultrasonic beam (F).

14 Claims, 3 Drawing Sheets

FOREIGN PATENT DOCUMENTS

| | | | |
|---|---|---|---|
| JP | 51-174151 | | 10/1984 |
| JP | 2001305115 | | 10/2001 |
| JP | 2002531978 | | 9/2002 |
| WO | WO 94/13411 | A1 | 6/1994 |
| WO | WO 00/33292 | A1 | 6/2000 |

OTHER PUBLICATIONS

Office Action in JP Patent Application 2006-540555 dated Jul. 20, 2010.

* cited by examiner

ULTRASONIC CONTACT TRANSDUCER WITH MULTIPLE EMITTING ELEMENTS AND MEANS OF BRINGING THESE ELEMENTS INTO CONTACT

CROSS-REFERENCE TO RELATED APPLICATION

This application claims priority based on International Patent Application No. PCT/FR2004/050589 filed on Nov. 16, 2004, entitled "Ultrasonic Contact Transducer with Multiple Emitting Elements and Means of Bringing These Elements into Contact" by Oliver Casula and Gerard Cattiaux, which claims priority of French Application No. 03 50842, filed on Nov. 17, 2003, and which was not published in English.

Technical Domain

This invention relates to an ultrasonic contact transducer with multiple ultrasonic emitting elements.

It is applicable particularly to medicine and non-destructive testing of mechanical parts, particularly of parts with a complex shape or an irregular surface condition, for example due to grinding or local addition of material.

State of the Prior Art

During an ultrasonic examination of some parts, an ultrasonic transducer is placed on a material for which the surface shape (geometry) changes depending on the zone considered of the material.

In this case, acoustic coupling between materials and the front face of the transducer is not optimal and the acoustic characteristics of ultrasonic beams transmitted are no longer maintained. The quality of inspections is then degraded.

Conventional techniques cannot completely check parts with a variable geometry.

For example, geometry variations such as elbows or take off points are frequent on pipe circuits. Yet parts with large geometric variations often have to resist the highest mechanical stresses, and therefore require the most frequent inspections.

In order to optimise the inspection of such areas, an ultrasonic transducer has been developed capable of adapting to parts with arbitrary shapes.

The first step was to guarantee optimum coupling between this transducer and the surface of a part. To achieve this, a monolithic transducer was replaced by a set of independent elementary transducers, this set being capable of deforming when in contact with the surface of the part. This thus improved the contact of the transducer with the surface of the part to be checked.

It should be noted that elementary transducers form an array with multiple elements for which the different acoustic characteristics need to be determined.

The next step is to transmit ultrasonic waves with the characteristics required for the inspection (refraction angle and focusing depth in the part) into the checked part. The next step is to impose emission delays to transducer elements using appropriate electronic means, so as to form the required ultrasonic beam.

The electrical signals output by ultrasonic sensors fitted on the transducer are then summated, these sensors possibly being the elements mentioned above that are used as elementary ultrasonic receivers.

Simulation software integrated into the electronic control means of the transducer is used to calculate delays that depend on the geometry and the component material of the checked part and the required characteristics for the ultrasonic beam, and to build up the elementary emitter excitation signal.

The shape of the part surface also needs to be known (and is a priori unknown). This is done by providing the transducer with means capable of outputting data that can be used to determine the local geometry of the checked part. These data are injected into the transducer control means in real time and the corresponding delay laws are recalculated. The result is thus an adaptive transducer that can be considered as being "intelligent".

Such a transducer is known by the document described below that should be referred to:

[1] WO 00/33292 A, "Transducteur ultrasonore de contact, à élément multiples" corresponding to U.S. Pat. No. 6,424, 597 A.

Flexible ultrasonic transducers are also described in the following documents:

[2] U.S. Pat. No. 5,913,825 A, "Ultrasonic probe and ultrasonic survey instrument", corresponding to JP 10 042 395 A.

[3] U.S. Pat. No. 5,680,863 A "Flexible ultrasonic transducers and related systems".

However, transducers described in documents [1] to [3] do not make it possible to keep an optimum coupling between them and complex parts, particularly when these transducers are displaced on the surface of such parts.

Presentation of the Invention

The purpose of this invention is to overcome this disadvantage.

To achieve this, this invention proposes an ultrasonic contact transducer with multiple elements, this transducer being characterised in that it comprises means of bringing the elements into contact with the surface of an object to be checked and means of determining the positions of the elements relative to the object, using the means of bringing the elements into contact, and in that each element is at least an ultrasonic emitter and the emitting elements are rigid and are assembled to each other mechanically so as to form an articulated structure.

None of documents [1] to [3] discloses or suggests such a combination of means.

In particular, in the transducer disclosed in document [1], nothing is provided to keep the elements in contact with the object that is being checked during displacements of the transducer during the check, and to assure coupling with the object.

The fact that the multiple elements of the transducer are rigid emitting elements and are mechanically assembled to each other so as to form an articulated structure, leads to a simplified and improved coupling between the emitters and an increased reliability since this coupling is achieved even if one emitter immediately adjacent to another is defective.

Preferably, the transducer can be moved relative to the object to be checked and has a deformable emitting surface formed by first faces of the elements and that will be brought into contact with the surface of this object and starting from which ultrasounds are emitted towards the object, control means being provided to generate excitation pulses of the emitting elements, the determination means being designed to define positions of the ultrasound emitting elements relative to the object during displacement of the transducer, processing means being provided to determine, starting from the positions thus determined, delay laws that emitting elements use to generate a focused ultrasonic beam for which the characteristics are controlled with respect to the object, and apply these delay laws to the excitation pulses, ultrasound receiving elements, possibly composed of the emitting elements, being designed to supply signals used to form images related to the object, the means for bringing into contact being Provided to bring the emitting elements into contact with the surface of the object and the determination means being provided to determine the positions of the emitting elements relative to the object through the means bringing the emitting elements into contact.

According to one preferred embodiment of the transducer according to the invention, the means of bringing the emitting elements into contact with the surface of the object comprise mechanical elements, each mechanical element including a portion that is free to move relative to a rigid portion of the transducer, a first end of this moving portion being capable of pressing emitting elements into contact with the surface of the object, and the means of determining the positions of the emitting elements relative to the object comprise first means provided to determine the positions of the emitting elements relative to the rigid portion of the transducer, by measuring the deformation of the emitting surface, and to output signals representative of positions thus determined, the first means comprising distance measurement means, provided to measure the distance between a second end of the moving portion of each mechanical element and an area of the rigid portion of the transducer and auxiliary processing means provided to determine the positions of the emitting elements with respect to the rigid portion of the transducer, using the second means provided to determine the position and orientation of this rigid portion with respect to the object and to output signals representative of the position and the orientation thus determined and third means provided to output the positions of the emitting elements with respect to the object using signals output by the first and second means.

Preferably, the first end of each moving portion is rounded.

According to one preferred embodiment of the invention, the rigid portion of the transducer comprises parallel holes in which the moving portions are respectively free to slide, and each mechanical element also includes elastic means capable of separating the first end of the moving portion corresponding to this mechanical element, from the rigid portion.

Preferably, each mechanical element also comprises a means (for example a ball bushing) in the hole corresponding to it, in which the moving portion of this mechanical element is free to slide with low friction.

According to one preferred embodiment of the transducer according to the invention, the distance measurement means are provided to optically measure the distance between the second end of the moving portion of each mechanical element and an area of the rigid portion, and comprise light emission means fixed to the rigid portion and designed to emit light towards this second end, this second end being capable of reflecting this light, and light reception means fixed to the rigid portion and provided to receive the light thus reflected, these reception means being capable of outputting signals representative of the distance between this second end and the corresponding zone.

According to a first particular embodiment of the transducer according to the invention, the light emission means and the light reception means include a photo-emitter and a photo-detector respectively, fixed to the rigid portion facing the second end.

According to a second particular embodiment of the transducer according to the invention, the light emission means include a first optical fibre to transmit light and send the light to the second end, and the light reception means include a second optical fibre to transmit light reflected by this second end.

The optical distance measurement means may use continuous light beams.

As a variant, the optical distance measurement means may use discontinuous light beams and particularly trains of light waves.

According to one particular embodiment of the invention, the means of bringing the emitting elements into contact also include a blade that covers second faces of the emitting elements, the first end of the moving portion of each mechanical element being capable of pressing emitting elements in contact with the surface of the object through the blade, this blade being capable of distributing forces applied by the moving elements on the emitting elements through the blade.

According to another particular embodiment, the emitting elements are rigid piezoelectric elements trapped in a flexible substrate that is passive with regard to ultrasounds.

In this case, the transducer preferably includes strips, the number of which is equal to the number of emitting elements and that are fixed to the face of the flexible substrate that is located facing the mechanical elements, each strip facing the moving portion of one of these mechanical elements, the first end of this moving portion being capable of pressing the emitting elements in contact with the surface of the object through the strip facing it.

BRIEF DESCRIPTION OF THE DRAWINGS

This invention will be described in the description of example embodiments given below, purely for guidance and in no way limitative, with reference to the attached drawings on which.

DETAILED PRESENTATION OF PARTICULAR EMBODIMENTS

Figure 1:
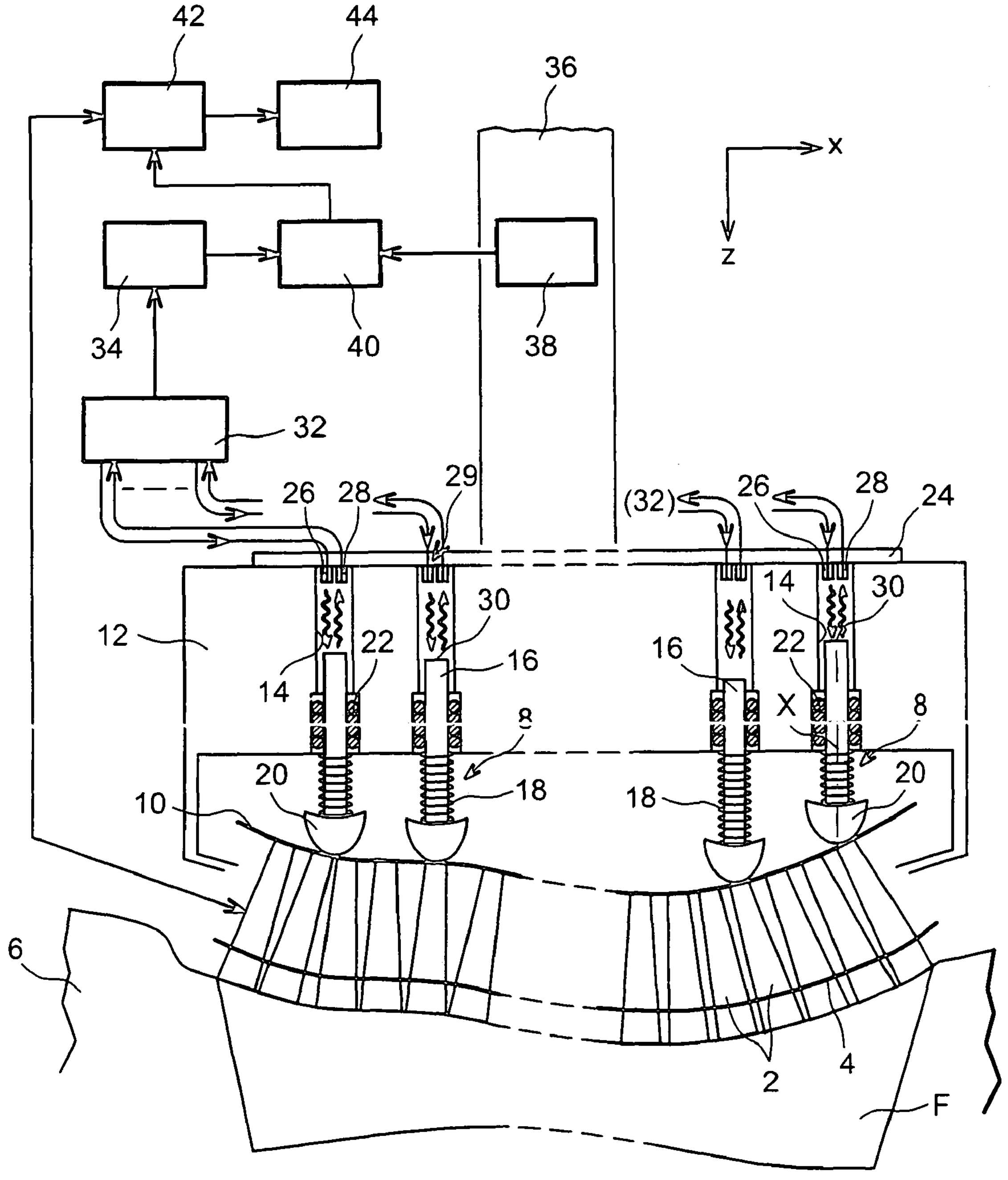
FIG. 1 is a diagrammatic view of a particular embodiment of the transducer according to the invention, using photo-emitters and photo-detectors.

The ultrasonic transducer according to the invention that will be described with reference to FIG. 1 is a flexible transducer provided with instrumentation adapted to inspection of compact parts, the shape of which is complex and difficult to access.

This transducer includes means for bringing into contact and profile measurement means (relief sensor).

The means for bringing into contact assure permanent acoustic coupling of the emitting elements of the transducer with the part to be checked as it is being scanned, while individual optical sensors measure the positions of spring pistons fitted on the transducer. These measurements are used to deduce the profile of the part to determine delay laws adapted to this part.

The means for bringing into contact and the means of measuring the deformation of the set of emitting elements in contact with the part are put together in order to minimise the total size of the transducer and to make it easy to grip. Putting these means together makes it possible for a sufficient number of optical sensors and adaptative electronic means to be integrated into the limited volume of the transducer.

FIG. 1 is comparable with FIG. 4 in document [1] that should be referred to.

In the example in FIG. 1, a linear strip type transducer is used that only accepts deformations in the plane of incidence of ultrasounds, namely plane (x, z) in FIG. 1.

This transducer includes ultrasonic emitter-receiver elements 2 forming a flexible assembly and connected through elastic and flexible means 4 for this purpose.

For example, these means 4 that assure mechanical cohesion of elements 2 and flexible assembly of these elements, can be

- a cable in the case of a two-dimensional flexible transducer, or
- a polymer resin substrate in the case of a flexible transducer with three dimensions.

More generally, as mentioned in document [1], it would be possible to use

- a flexible piezoelectric polymer strip and an array of electrodes placed adjacent to each other, obtained by metallic deposition, or
- a set of rigid piezoelectric elements cast into a flexible substrate that is inert with regard to ultrasounds, or
- a set of rigid ultrasound elements mechanically assembled so as to obtain an articulated structure.

In the example in FIG. 1, a known linear and deformable multi-element strip is used, for which the piezoelectric elements 2 are trapezoidal in shape.

The transducer comprises spring pistons 8 and a metallic foil 10 that forms a strip-spring, to keep these piezoelectric elements 2 in contact with the part to be checked 6. This strip-spring is placed on the set of back faces of elements 2, each of which has a front face or active face that is in contact with the surface of the part to be checked 6, the set of active faces forming a deformable emitting surface.

The metallic full 10 distributes vertical forces applied by the spring pistons and also enables the elements 2 to tilt transversely without being blocked by the pistons 8.

The transducer in FIG. 1 also comprises a rigid box 12 to which the multi-element strip is fixed. This box 12 comprises a set of parallel holes 14 with coplanar axes, the number of holes being equal to the number of spring pistons.

Each spring piston 8 comprises a moving part 16 capable of sliding in the corresponding hole and a spring 18 through which this moving part 16 passes and is included between the box 12 and the end 20 of this moving part, that is the closest to the elements 2.

This end 20 is wider than the remaining part of the moving part to retain the spring 18. This end 20 is also rounded, and preferably hemispherical as can be seen in FIG. 1, to optimise pressure applied on the back faces of the elements 2 through the metallic foil 10.

When the transducer is applied in contact with the part to be checked 6, the springs 18 are compressed and therefore tend to separate the ends 20 of the box 12 such that the elements 2 are kept in permanent contact with the part 4.

A ball bushing 22 is placed in each hole 14, which has the same axis as this hole and inside which the moving part 16 of the piston corresponding to this hole is free to slide. This ball bushing 22 is designed to improve displacement of this moving part in the hole, to reduce friction during this displacement and to eliminate the clearance between this moving part and the hole.

The positions of elements 2 with respect to the part 6 as the transducer is being displaced are determined through spring pistons.

To achieve this, the upper part of the box 12 includes a (rigid) plate 24 that closes the upper ends of the holes 14 and that forms a geometric reference for position measurements of elements 2. In each hole 14, a light emitting diode 26 and a photodetector 28 are fixed to this plate 24 in an area 29 of the plate, facing the other end 30 of the moving part 16 of the piston corresponding to this hole.

This other end 30 is perpendicular to the X axis that is common to the hole 14 and to this moving part 16 and it is polished or made reflecting for example by polishing, to form a mirror. This mirror reflects a fraction of a light beam emitted by the light emitting diode 26. The quantity of reflected light energy is a decreasing function of the separation between the moving part and the light emitting diode 26.

The light beam reflected by the mirror is picked up by the photo-detector 28 that is placed adjacent to the diode 26. This photo-detector then outputs a photo current that depends on the distance between the end 30 of the moving part 16 and the photodetector (and therefore the plate 24) and consequently the position of elements 2 with respect to the rigid part 12 (knowing the length of the moving parts 16).

Programmable electronic means 32 are provided to control light emitting diodes 26, to digitise the photo-current output from each photodetector 28 and to convert this photo-current into a displacement.

However, the curve of variations of the displacement as a function of the photo-current is not linear such that a calibration is necessary.

This calibration is made during an acquisition step during which the photo-current is measured for several calibrated positions of the moving part 16 of each piston 8, over the entire range of this piston, in other words the entire displacement possible for this piston.

After calibrating each photo-detector, it is possible to convert the measured photo-current into a displacement.

The respective positions of the photo-detectors with respect to the back faces of the elements 2 are known, therefore interpolation methods are used to reconstruct the profile described by the back faces of the elements. Projection operations then provide the coordinates of the surface of the part 6.

More precisely, the means 32 are also designed to determine the positions of the back faces of elements 2 relative to the rigid box 12.

Auxiliary processing means 34 determine the positions of the active faces of elements 2 relative to the box as a function of the positions of back faces thus determined (see document [1]).

An articulated mechanical arm 36 is used to obtain the position and orientation of the transducer in the fixed coordinate system of the part to be checked 6. Sensors 38 fitted on the arm 36 are used to locate this transducer in space and to measure its orientation during its displacement relative to part 6, as indicated in document [1].

FIG. 1 also shows means 40 that, depending on the positions output by the means 34 and as a function of the position and orientation output by the sensors 38, determine the positions of the transducer relative to part 6.

The Figure also shows control and processing means 42 provided to generate excitation pulses of the elements 2, determine delay laws using the positions thus determined, to enable elements 2 to generate a focused ultrasonic beam F, for which the characteristics are controlled with respect to part 2, and apply these delay laws to the excitation pulses.

The elements 2 then output signals to means 42 also designed to form images related to the part 6, using these signals.

These images are displayed on a screen 44.

As described in document [1], inertial sensors can also be used to obtain the position and orientation of the transducer.

Light emitting diodes can be controlled so as to emit continuous light beams or discontinuous light beams, and particularly light pulses.

The means 32 may be designed to query the required photodetecor 28 by controlling the corresponding light emitting diode.

Figure 2:
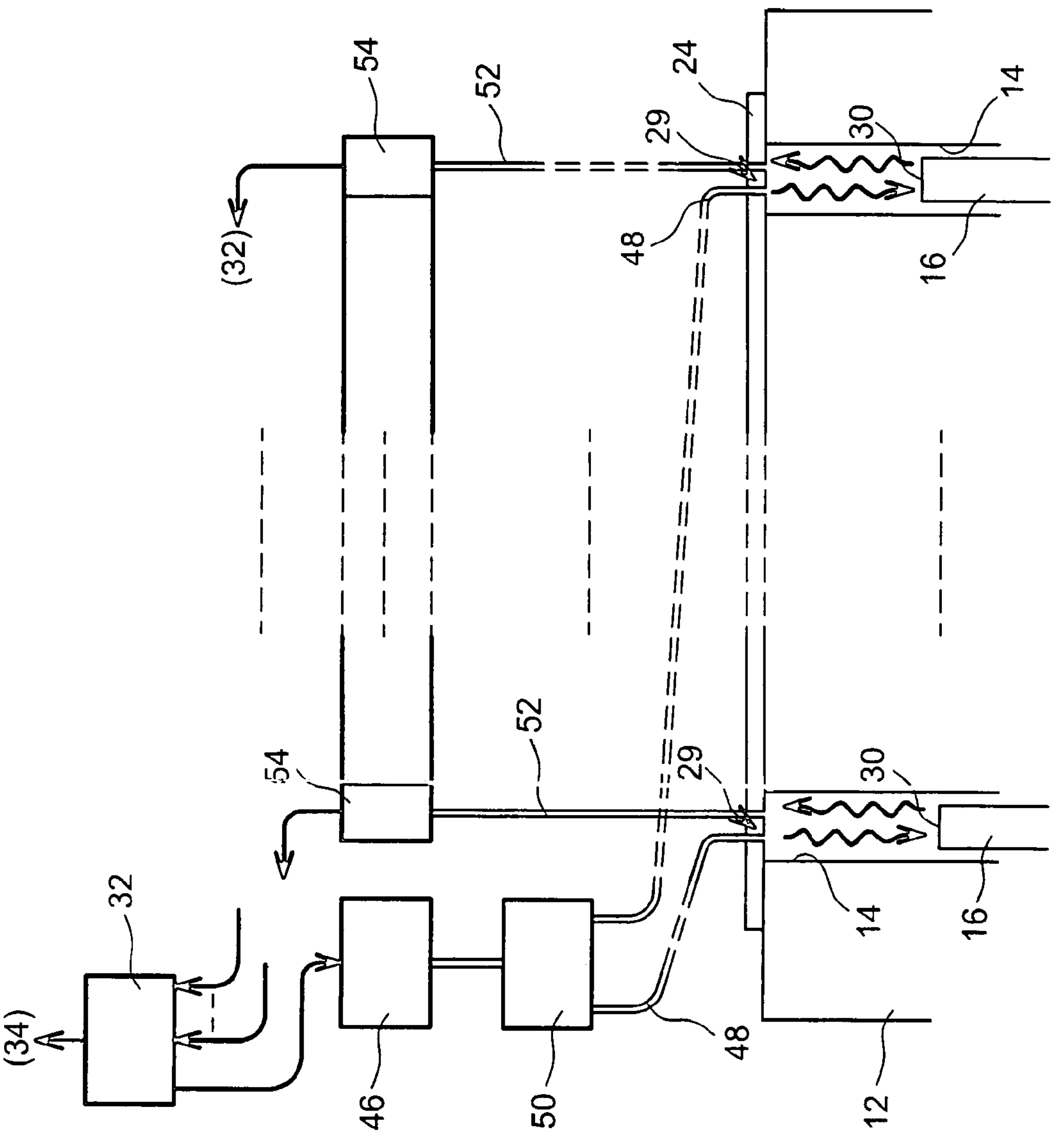
FIG. 2 is a diagrammatic partial view of another particular embodiment using optical fibres.

FIG. 2 is a partial diagrammatic view of a variant of the transducer in FIG. 1. In this variant, optical fibres are used to transmit light to the corresponding second ends of the moving parts of pistons and to transmit light reflected by these second ends.

In the example in FIG. 2, means 32 control a light source 46 from which light is sent to the ends of the optical fibres 48, the number of the fibres being equal to the number of pistons, through an optical coupler 50. The other ends of the fibres 48 open up into holes 14 as shown in FIG. 2, to be able to “illuminate” the reflecting ends 30 of the moving parts 16.

A light source per optical fibre can also be used.

It can be seen that each of the said other ends of the fibres is fixed to zone 29 of the plate 24 facing the corresponding end 30.

Other optical fibres 52 are also provided, the number of which is equal to the number of fibres 48 and for which ends open into the holes 14, adjacent to the ends of fibres 48, and are fixed to zones 29 respectively facing the corresponding ends 30.

The fibres 52 make it possible to recover light reflected by the reflecting ends 30 of the moving parts 16 and to transmit this light to the corresponding photodetectors 54. These photodetectors then generate photo-currents that are transmitted to the means 32.

In the examples according to the invention that have just been described, the distance measurement means used particularly to detect piston displacements consist of optical means, therefore enabling optical detection of these displacements.

However, these optical means may be replaced by magnetic means.

In one example not shown, each diode 26-photodetector 28 set in FIG. 1 is replaced by a Hall effect sensor and a magnet is fixed onto the end 30 of the moving part of the corresponding piston.

The Hall effect sensor is thus capable of outputting a signal that depends on the distance between this sensor and this magnet. Thus also, the required distance can be measured by replacing means 32 in FIG. 1 by appropriate means of controlling the sensor and processing signals output by it.

In one variant of this example (not shown), the magnet is fixed to the plate 24, adjacent to the Hall effect sensor, in the corresponding hole 14, and at least the end 30 of the moving part of each piston is made from a magnetic material such as steel.

The magnetic field detected by each sensor is then disturbed by the corresponding end 30 and the sensor also outputs a signal that depends on the distance between this end 30 and this sensor.

Furthermore, examples according to the invention that are given above use ultrasound emitting and receiving elements. Those skilled in the art can adapt these examples to the case of transducers including elements designed only to emit ultrasounds and other elements designed only to receive ultrasounds.

Furthermore, in these examples, transducers including a linear strip of ultrasound elements are used, but the invention is not limited to such transducers. As in document [1], those skilled in the art will be able to adapt the examples given to matrix transducers.

It is then necessary to associate parallel rows of spring pistons with such a matrix transducer, these rows being of the type described above with reference to FIG. 1, and to include a metallic foil on the back faces of elements fitted on the transducer.

Figure 3:
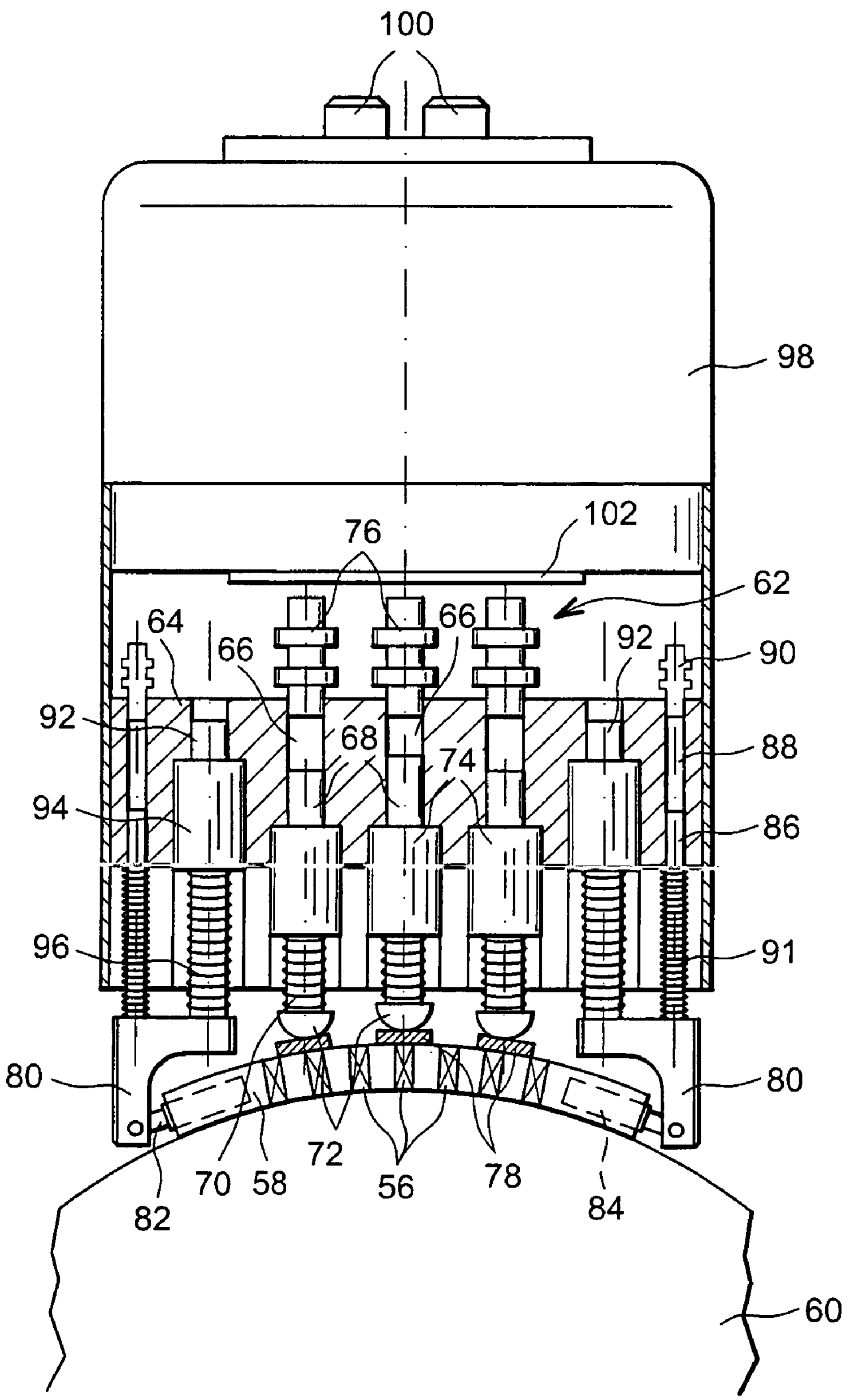
FIG. 3 is a diagrammatic sectional view of a matrix ultrasonic transducer according to the invention.

We will now describe another example of the invention with reference to FIG. 3, that is useable more particularly in the case in which the ultrasound elements form a matrix rather than a single row.

The transducer according to the invention that can be seen in section in FIG. 3, comprises a matrix of ultrasound emitter-receiver elements 56 that are trapped in a flexible resin substrate 58, this substrate being passive with regard to ultrasounds.

In order to keep the piezoelectric elements 56 in contact with a part to be checked 60 that is convex in the example in FIG. 3, the transducer includes a matrix assembly of spring pistons 62 and a rigid box 64 for which the flexible substrate 58 is fixed in a manner that will be explained below.

The box 64 comprises a matrix assembly of parallel holes 66 that are associated with corresponding spring pistons. Each spring piston comprises a moving part 68 that is capable of sliding in the corresponding hole, and a spring 70 through which this moving part passes and that is included between the box 64 and the end 72 of this moving part, that is closest to the elements 56. This end is rounded and is preferably hemispherical, as is the case in FIG. 1.

Ball bushings 74 are still provided to improve displacement of the moving parts 68 in the corresponding holes 68 as is shown in FIG. 3.

In the example in this FIG. 3, the positions of elements 56 from part 60 are determined during displacement of the transducer by means of spring pistons, and to achieve this each piston is associated with a position sensor 76 as is shown in the example in FIG. 1.

The example in FIG. 3 also uses an optical sensor including a light emitter towards the piston and a light receiver receiving light reflected by the back end of the moving part 68 of this piston, made reflecting for this purpose.

Preferably, strips 78 are fixed to the upper surface of the flexible substrate 58, facing the corresponding hemispherical ends 72 of the pistons, and thus form a matrix assembly. These strips are used to distribute the vertical forces applied by the spring pistons. These strips preferably form thin metallic disks with a diameter equal to the diameter of the hemispherical ends.

The transducer in FIG. 3 also comprises four supports 80, that for example form angles and are at 90° from each other, only two of these supports being visible in FIG. 3. Each of these supports is fixed to the flexible substrate 58 through a rod 82 articulated with respect to this support. This rod 82 is capable of sliding in an insert 84 that is embedded in the flexible substrate 58 made of resin.

Each of these supports 80 is also fixed to one end of an axis 86. The other end of these axes can slide in a hole 88 passing through the rigid box as shown in FIG. 3. This hole is parallel to the holes 66 in which the moving parts of the pistons slide.

The use of rods 82 sliding in the inserts 84 prevents the appearance of lateral tensions that could tear the substrate 58.

Furthermore, the mechanical system including supports 80, rods 86, inserts 84 and axes 82, prevents any rotation of the flexible substrate 58 and therefore the set of elements 56.

If required, the movement of the flexible substrate 58 with respect to the box 64 can be measured by means of position detectors 90, such as detectors 76, that can be used to measure the travel distance of the axes 86, used to hold the flexible substrate.

FIG. 3 also shows the springs 91 through which the rods 86 pass and that are included between the supports 80 and the rigid box 64.

Each of these rods 86 can also be associated with another rod 92 capable of sliding in the rigid box 64 through a ball bushing 94 and fixed to the corresponding support 80. As can be seen in FIG. 3, a spring 96 is then provided between this support 80 and the rigid box 64, through which this other rod 92 passes.

The rigid box 64 may be fixed to an electronic box 98 that can also be used as a handle for the transducer. Elements 100 can be seen in the upper part of this electronic box 98, through which electrical cables (not shown) exit from this box. These cables are used for the transport of signals output by the transducer and by position sensors 76.

A base 102 can be seen designed to hold electrical connectors (not shown), at the bottom of this electronic box 90, output from the different ultrasound elements 56 and to connect these connectors to electronic means contained in the box 98, and used to control these elements 56 and to process signals output by these elements.

The rods 92 associated with the ball bushings 94 and springs 96 could be replaced by simple angles fixed to supports 80 and capable of sliding in holes provided for this purpose in the rigid box 94.

The various electrical connections necessary for the transducer in FIG. 3 are not shown, for reasons of clarity.

Similarly, the various signal control and processing means necessary for operation of this transducer are not shown. These means that correspond to a matrix transducer may be determined by those skilled in the art, making use of means similar to those described with reference to FIG. 1 for a linear transducer.

The invention claimed is:

1. An ultrasonic contact transducer with multiple elements, said transducer comprising:

means for bringing the elements into contact with the surface of an object to be checked; and means for determining the positions of the multiple elements relative to the object, wherein each of the multiple elements is at least an ultrasound emitting element, and wherein the ultrasound emitting elements are rigid and are assembled to each other mechanically so as to form an articulated structure.

2. The transducer according to claim 1, in which the transducer further comprising:

control means for generating excitation pulses of the ultrasound emitting elements;

processing means for:

a) determining, starting from the positions thus determined, delay laws that the ultrasound emitting elements use to generate a focused ultrasonic beam for which the characteristics are controlled with respect to the object, and b) applying these delay laws to the excitation pulses, ultrasound receiving elements, constituted by the ultrasound emitting elements, configured to supply signals used to form images related to the object.

3. An ultrasonic contact transducer with multiple elements, said transducer comprising:

ultrasound emitting elements including mechanical elements, each mechanical element including a moving portion that is free to move relative to a rigid portion of the transducer, a first end of the moving portion configured to press a corresponding ultrasound emitting element into contact with the surface of the object;

position determining unit of multiple elements, including:

first unit, for determining the positions of the ultrasound emitting elements relative to the rigid portion of the transducer by measuring the deformation of the emitting surface, and for outputting signals representative of the positions thus determined, the first unit comprising:

distance measurement unit for measuring the distance between a second end of the moving portion of each mechanical element and an area of the rigid portion of the transducer and auxiliary processing unit for determining the positions of the ultrasound emitting elements with respect to the rigid portion of the transducer, using the distances thus determined, second unit for determining the position and orientation of the rigid portion with respect to the object and for outputting signals representative of the position and the orientation thus determined and third unit for outputting the positions of the ultrasound emitting elements with respect to the object using signals output by the first and second unit.

4. The transducer according to claim 3, wherein the first end of each moving portion is rounded.

5. The transducer according to claim 3, wherein the rigid portion of the transducer comprises parallel holes in which the moving portions are respectively free to slide, and each mechanical element also includes elastic means for separating the first end of the moving portion corresponding to this mechanical element, from the rigid portion.

6. The transducer according to claim 5, wherein each mechanical element also comprises a means for reducing friction for the moving portion.

7. The transducer according to claim 3, wherein the distance measurement unit is configured to optically measure the distance between the second end of the moving portion of each mechanical element and an area of the rigid portion, and comprises:

light emission means, fixed to the rigid portion, for emitting light towards the second end, the second end being capable of reflecting the emitted light, and light reception means, fixed to the rigid portion, for receiving the light thus reflected, the light reception means being capable of outputting signals representative of the distance between this second end and the corresponding zone.

8. The transducer according to claim 7, wherein the light emission means and the light reception means include a photo-emitter and a photo-detector respectively, fixed to the rigid portion facing the second end.

9. The transducer according to claim 7, wherein the light emission means include a first optical fiber to transmit light and send the light to the second end, and the light reception means include a second optical fiber to transmit light reflected by this second end.

10. The transducer according to claim 7, wherein the distance measurement means uses continuous light beams.

11. The transducer according to claim 7, wherein the distance measurement means uses discontinuous light beams and particularly trains of light waves.

12. The transducer according to claim 3, wherein the ultrasound emitting elements include a blade that covers second faces of the ultrasound emitting elements, the first end of the moving portion of each mechanical element being capable of pressing ultrasound emitting elements in contact with the surface of the object through the blade, the blade being capable of distributing forces applied by the moving elements on the emitting elements through the blade.

13. The transducer according to claim 3, wherein the ultrasound emitting elements are rigid piezoelectric elements trapped in a flexible substrate that is passive with regard to ultrasounds.

14. The transducer according to claim 13, further comprising strips, the number of which is equal to the number of ultrasound emitting elements and that are fixed to the face of the flexible substrate that is located facing the mechanical elements, each strip facing the moving portion of one of these mechanical elements, the first end of this moving portion being capable of pressing the ultrasound emitting elements in contact with the surface of the object through the strip facing it.

* * * * *